United States Patent
Kindler et al.

(10) Patent No.: US 7,291,133 B1
(45) Date of Patent: Nov. 6, 2007

(54) DEVICE FOR THE METERED ADMINISTRATION OF A FLUID DRUG

(75) Inventors: Beat Kindler, Hasle-Rüegsau (CH); Daniel Peter, Niederwangen (CH); Ueli Haueter, Grosshöchstetten (CH); Reto Aeschlimann, Aefligen (CH)

(73) Assignee: Disetronic Licensing AG, Burgdorf (CH)

( * ) Notice: Subject to any disclaimer, the term of this patent is extended or adjusted under 35 U.S.C. 154(b) by 0 days.

(21) Appl. No.: 09/092,546

(22) Filed: Jun. 5, 1998

(30) Foreign Application Priority Data

Jun. 5, 1997 (DE) .............................. 197 23 648

(51) Int. Cl.
*A61M 5/00* (2006.01)
*A61M 5/14* (2006.01)

(52) U.S. Cl. ..................... 604/247; 604/256
(58) Field of Classification Search ............ 604/533, 604/246–7, 256, 115, 118–9, 131, 86–91, 604/240, 241, 247, 242, 236, 200–206
See application file for complete search history.

(56) References Cited

U.S. PATENT DOCUMENTS

| | | | |
|---|---|---|---|
| 3,601,151 A * | 8/1971 | Winnard ..................... 137/846 |
| 3,759,425 A * | 9/1973 | Lee ............................ 222/309 |
| 3,884,228 A | 5/1975 | Hahn ......................... 128/214 |
| 4,143,853 A * | 3/1979 | Abramson ............... 251/149.1 |
| 4,562,751 A | 1/1986 | Nason et al. |
| 4,615,693 A | 10/1986 | Paradis et al. |
| 4,681,132 A | 7/1987 | Lardner |
| 4,731,060 A * | 3/1988 | Catalano .................... 604/254 |
| 4,919,167 A | 4/1990 | Manska |
| 4,935,009 A * | 6/1990 | Caldwell et al. ............ 604/507 |
| 4,969,874 A * | 11/1990 | Michel et al. ............... 604/140 |
| 5,084,060 A | 1/1992 | Freund et al. ............... 606/192 |
| 5,209,739 A | 5/1993 | Talalay ....................... 604/195 |
| 5,336,183 A | 8/1994 | Greelis et al. ................ 607/97 |
| 5,453,097 A * | 9/1995 | Paradis ....................... 604/246 |
| 5,616,133 A * | 4/1997 | Cardenas .................... 604/187 |
| 5,743,872 A | 4/1998 | Kelly .......................... 604/49 |
| 5,788,673 A | 8/1998 | Young et al. ............... 604/131 |
| 5,807,323 A * | 9/1998 | Kriesel et al. ................ 604/89 |

(Continued)

FOREIGN PATENT DOCUMENTS

AU 5861273 1/1975

(Continued)

*Primary Examiner*—Nicholas D. Lucchesi
*Assistant Examiner*—Matthew F DeSanto
(74) *Attorney, Agent, or Firm*—Dorsey & Whitney LLP

(57) ABSTRACT

A device for the metered administration of a fluid drug. The device has a container having a piston for administering the fluid drug through an outlet of the container, a catheter connected to the outlet of the container, the catheter having a front end facing away from the outlet and being connected to an injection needle, and a valve positioned between the outlet and the injection needle in a flow cross section of the fluid drug, the valve having an inlet end adjacent the outlet and an outlet end adjacent the injection needle, wherein the valve permits flow of the fluid drug through the valve from the outlet to the injection needle when a fluid pressure exerted on the inlet end of the valve exceeds a pressure on the inlet end caused by the dead weight of the fluid drug.

12 Claims, 13 Drawing Sheets

U.S. PATENT DOCUMENTS 5,826,621 A     10/1998   Jemmott
5,827,244 A  *  10/1998   Boettger .................. 604/533
5,853,397 A     12/1998   Shemesh et al.

FOREIGN PATENT DOCUMENTS

| | | |
|---|---|---|
| DE | 2819900 | 11/1978 |
| DE | 3922291 | 11/1990 |
| DE | 196 33 530 A1 | 2/1998 |
| DE | 19717107 | 11/1998 |
| EP | 0143895 | 4/1986 |
| WO | WO9415660 | 7/1994 |
| WO | WO 9627398 | 9/1996 |
| WO | WO97/02059 | 1/1997 |
| WO | WO9700091 | 1/1997 |

* cited by examiner

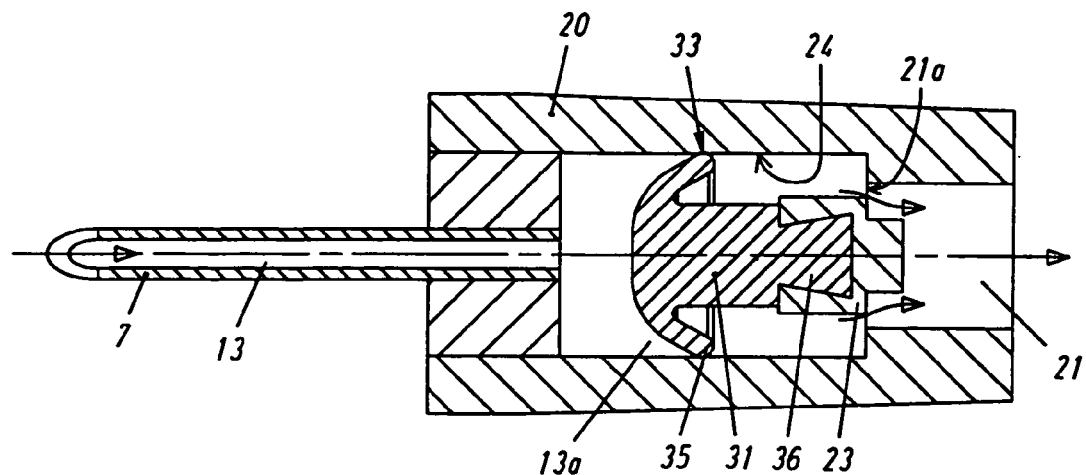
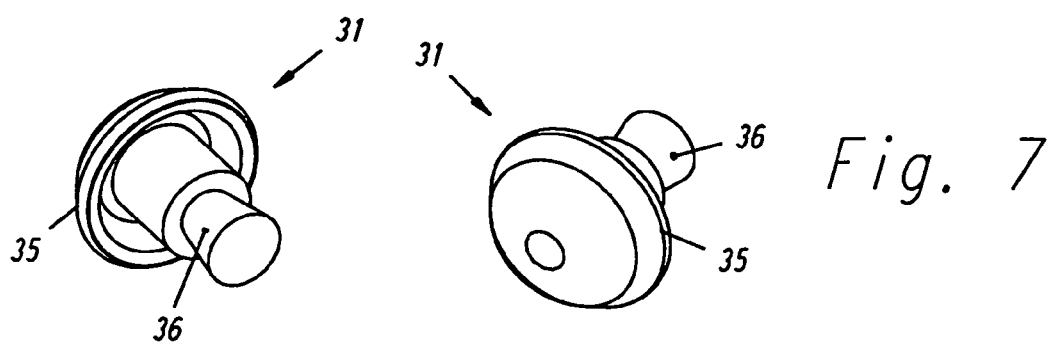
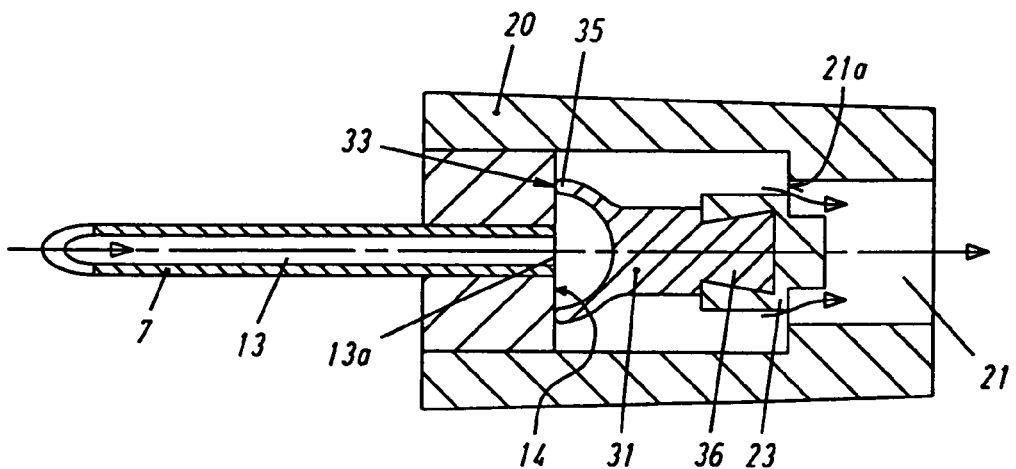
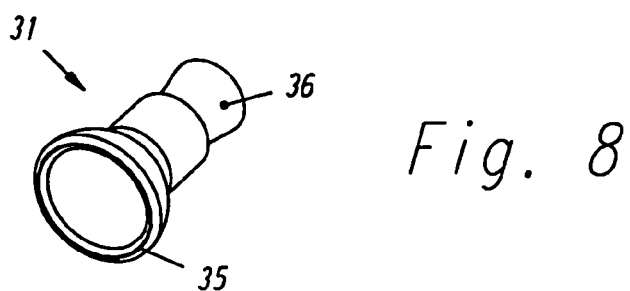
Fig. 7
Fig. 8

DEVICE FOR THE METERED ADMINISTRATION OF A FLUID DRUG

This application claims the priority of German Patent Application No. 197 23 648.0, filed Jun. 5, 1997, which is incorporated herein by reference.

BACKGROUND OF THE INVENTION

1. Field of the Invention

The invention refers to a device for the metered administration and in particular the infusion of a fluid drug, comprising a container from which upon advancing a piston for administering said fluid drug the fluid drug is displaced in dosed manner through an outlet and a catheter connected to an outlet of said container, whose front end facing away from the outlet is connected to an injection needle, wherein a valve is positioned between the outlet and the injection needle in a flow cross section of the fluid drug and the valve, in order to prevent a self-discharge, only permits the flow to the front end of the catheter if the fluid pressure exerted in this direction exceeds a pressure on the valve caused by the dead weight of a fluid column in the device.

2. Description of the Related Art

In known infusion systems, the drug to be administered is stored in a container, normally an ampule, containing a carrier fluid in which the drug is dissolved—hereinafter referred to as fluid drug—between a movable piston and a container outlet. The rear end of a catheter is connected to the container outlet. The front catheter end contains an injection needle for administering the fluid drug into a human or animal body, which in most cases often remains there for the administration over several days. Where the fluid drug container is located at a greater height than the front end of the catheter or the needle, there is the danger that with sufficient height difference between the container and the front end of the catheter, the container could discharge itself as a result of the force of the fluid column.

In case of insulinisation, where portable infusion devices are used, i.e. pump devices, used catheters can exceed a length of 1 m. The longest catheter currently used with an infusion device has a length of some 1.1 m. Where the device with the container is vertically arranged above the user, i.e. during night time, this creates a hydrostatic base pressure of approx. 0.1 bar, if apart from the purely statistical pressure due to the dead weight of the fluid drug, no further effects such as frictional losses, discharge or capillary effects are considered and a density equal to that of water is assumed for the fluid drug.

In order to prevent the undesired discharge as a result of the fluid column pressure, the side friction between the piston displaceably arranged in the container and the container wall could be increased, which, however, would lead to other disadvantages. As a further solution the piston could be attached to the driven member, thus preventing a lowering of the fluid surface in the container and consequently a self-discharge. In known systems, the piston is screw-fitted to the driven member. This, however, adversely affects the cost of the device. This solution can also not be used for ready-to-use ampules as the piston is not prepared for a screw connection.

SUMMARY OF THE INVENTION

The invention has the task to provide a device for the metered administration of a fluid drug from a fluid container in which an uncontrolled discharge under conditions experienced in the daily operation is prevented.

This task is solved by a valve which is positioned between the outlet and the injection needle in a flow cross section of the fluid drug and which valve, in order to prevent a self-discharge, only permits the flow to the front end of the catheter if the fluid pressure exerted in this direction exceeds a pressure on the valve caused by the dead weight of a fluid column in the device.

The invention is based on a device for the dosed administration of a fluid drug, in which the drug is held in a container from which it is displaced in a dosed manner for administration by the advancing of a piston, movably held in the container, towards a container outlet. The rear end of such a catheter is directly connected to the outlet of the container via an outlet section or piece provided for the connection of a catheter. Usually, hose-shaped catheters are used. Rigid catheters could, however, also be used. The free front end of the catheter is connected to an injection needle for the administration of the drug or can be connected to said needle. The term administering refers in this instance to infusions and injections, as well as a combination of both types of administration. The invention is particularly relevant for the use with infusion elements or devices. These preferably consist of portable devices for insulin treatment.

According to the invention a valve for administering a drug is positioned in a flow cross-section of the fluid drug between the container outlet and the injection needle. In order to prevent a self-discharge, the valve is dimensioned in such a way that a flow to the front end of the catheter is only possible if the fluid pressure in this direction exceeds a pressure on the valve caused by the dead weight of a fluid column in the device. In case of a mass produced device for a whole range of catheters of different lengths, the valve is dimensioned for the use with the longest catheter, i.e. for the maximum possible fluid column.

The valve is advantageously designed as a one-way valve, ideally preventing a reflow into the container. Preferably, the valve is a return valve.

In order to impede the metered administration of the drug as little as possible whilst at the same time safely preventing a self-discharge, the valve is preferably designed in such a way that it only permits the flow to the front end of the catheter if the fluid pressure in this direction exceeds the maximum possible pressure of the fluid column, preferably multiplied with a safety factor. As in this case the valve is used in medical applications, the safety factor should preferably have a value of 3. With a maximum catheter length of approx. 1 m and a negligible fluid column in the container, the maximum fluid pressure at the free end of the catheter is approx. 0.1 bar, so that the valve in this case is designed to open only if a fluid pressure of 0.3 bar is exceeded. This is also the dimension for the preferred application in a portable infusion pump.

Although the valve could, in principle, be arranged at any point between the container outlet and an injection needle, it is preferably arranged as close as possible to the outlet of the container. In this arrangement the valve will, in case of a return valve, also effectively prevent the reflow into the container.

To accommodate the valve an outlet piece could, for instance, be arranged in the area of the container outlet.

According to a particularly preferred embodiment, the valve is arranged in a housing serving as a connection section for the catheter. The valve can consequently be easily replaced together with the catheter.

The valve contains a valve body as a sealing element, preferably made from elastic material, sealing in its assembled condition a feed line, i.e. sealing its at least one opening. The feed line directly in front of the valve body can be a connecting needle, piercing a membrane during the connection of the catheter to the container outlet and thus providing a fluid connection. The last section of the feed pipe with the aperture sealed by the valve body, can also be formed by the said housing in which, for instance, such a connection needle is accommodated.

The sealing of the flow cross section can be achieved by the effect of a sealing lip on a narrower, exactly defined contact surface formed at the valve body or at the feed line. Achieving the sealing with at least one sealing lip surrounding the at least one aperture of the feed line, has the advantage that the pressure at which the valve opens and closes, can be defined. The feed pipe arrangement has the advantage of a simple valve housing production.

In a further embodiment, the elastic valve body is a hollow cylinder and is attached to the feed line like a hose. The at least one sealable aperture of the feed line is arranged in a surface area of the feed pipe. The feed pipe and the valve body arranged over the feed pipe, co-operate in the manner of a bicycle tube valve.

A particular simple design of a valve body is a sealing stopper made from elastic material, closing the flow cross-section of a fluid drug in a stopper-like fashion. The sealing stopper can contain a pre-manufactured aperture, which during its application remains, however, closed until the said, sufficiently high fluid pressure is exerted on the sealing stopper. In order to simplify the production of the valve, the aperture is only created after the installation of the sealing stopper in the housing, by a connecting needle which when inserted into the housing initially completely pierces the sealing stopper and is then retracted to some extent so that the created aperture is sealed again by the elastic mass of the sealing stopper.

Further valves according to the invention contain an elastic valve body operating in the manner of a heart valve.

Furthermore, also a spring-loaded valve body, containing a pressure spring, could be used.

BRIEF DESCRIPTION OF THE DRAWINGS

The preferred embodiments of the invention are explained below with reference to the figures in which:

FIGS. 2–21 represent alternative embodiments of the valve and its arrangement according to FIG. 1.

DESCRIPTION OF THE PREFERRED EMBODIMENTS

Figure 1:
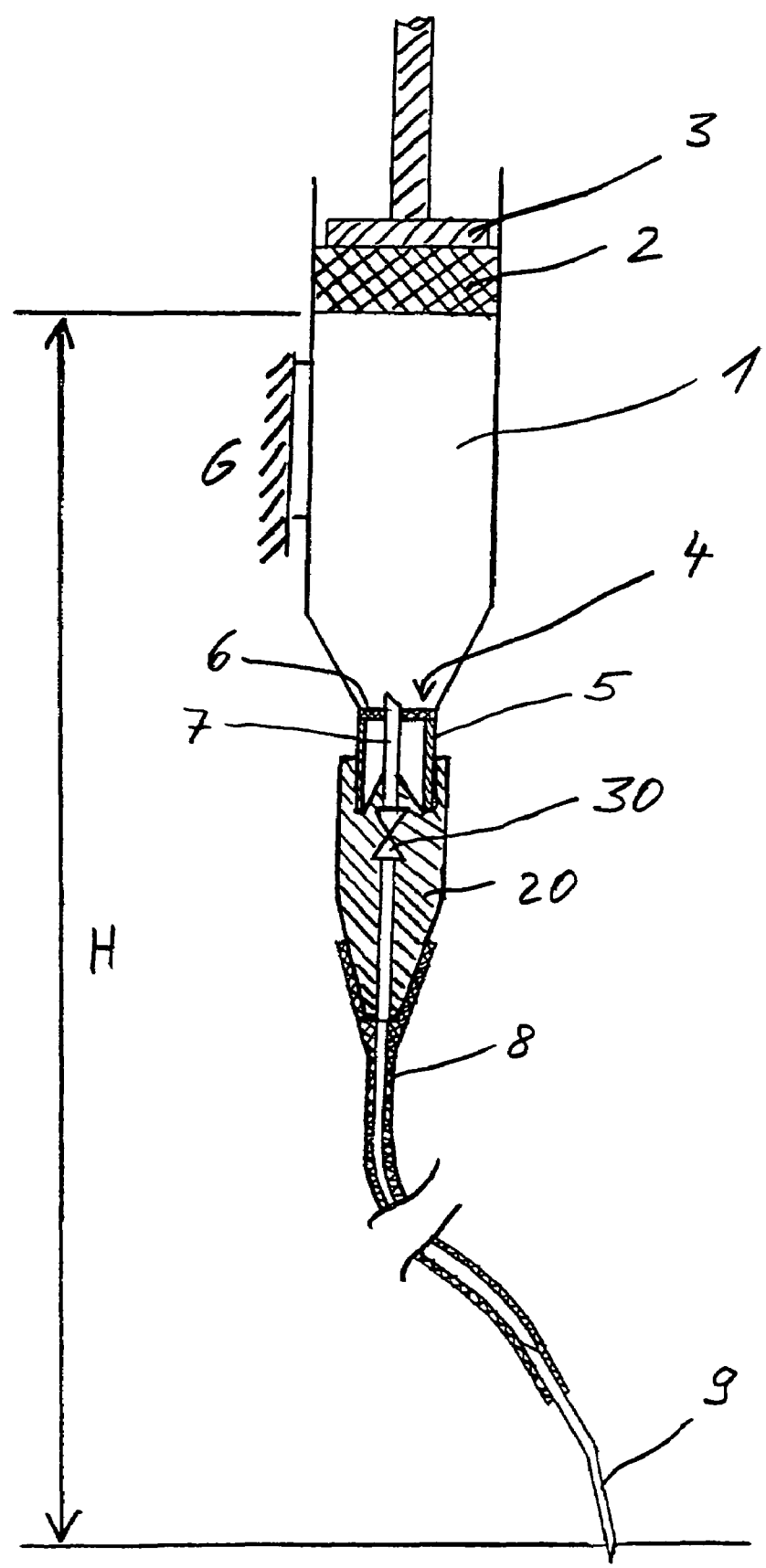
FIG. 1 represents a device according to the invention, including a valve, preventing an uncontrolled discharge of a drug

FIG. 1 represents a device for the metered administration of a fluid drug. The shown embodiment can be used as a device for an infusion or an injection system. For the purpose of a preferred application only infusion and in particular the infusion of insulin will be referred to below.

The insulin dissolved in a carrier fluid is contained in a container or an ampule 1, secured 21 on a rack or in a housing G. The ampule 1 accommodates a freely displaceable piston 2. By advancing the piston 2 in a direction of an outlet 4 of the container 1, insulin fluid is displaced from the ampule 1. A driven member 3 of a preferably motorized drive element for the piston 2 affects the advancement of the piston by exerting pressure on the rear side of said piston. There is no interlocking or material connection between the driven member 3 and the piston 2. Piston 2 is only held in the ampule 1 by the frictional forces of the side wall required to achieve imperviousness. The advancing movement of the driven member 3 and thus of the piston 2 is exactly controlled to discharge the insulin in a finely dosed manner through the outlet 4.

The outlet 4 is sealed by a fluid-proof membrane 6 before the first use of the ampule 1. Upon connection of an infusion catheter 8, the membrane 6 is pierced by a connecting needle 7 that is arranged in the housing 20. The housing 20 serves as a connecting section for the catheter 8. The rear end of the catheter is attached to the conically shaped front end of the housing or of the connecting section 20. The rear end of the connecting section 20 is screwed on or screwed in or fixed with a snap-in lock to the outlet section 5, extending the outlet 4. An infusion needle 9 is connected to the front, free end of the catheter 8.

In this arrangement in which the infusion needle 9 is inserted by the patient into the skin and in which his pump unit including the ampule 1 has been fixed or stored with a height differential H above the injection area, for instance during night time, the pressure of the fluid column between the front end and the infusion needle 9 and the fluid surface in ampule 1 created by the height differential H is constantly exerted on the front end of the injection needle 9. As a result of this pressure, insulin would continuously be released at the front end of the infusion needle 9.

In order to prevent this, a passive one- or two-way valve 30, and in particular a return valve is arranged in the flow cross-section of the insulin fluid within the connecting section 20. The valve 30 only permits a flow from the outlet 4 into the catheter 8 if the fluid pressure in the direction of the infusion needle exceeds the pressure of the fluid column with a maximum height differential H by a stipulated safety factor. In cases where the valve 30 is designed as a passive one-way valve, i.e. a simple return valve, it also prevents the reflow of the fluid drug into the ampule 1 and further increases the functional safety of the pump.

Figure 2:
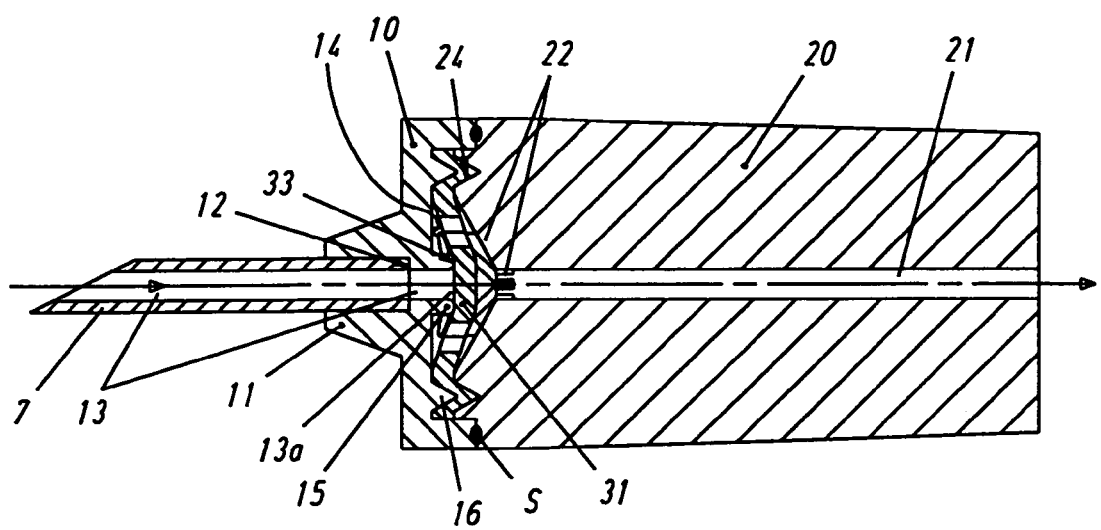
Figure 2:
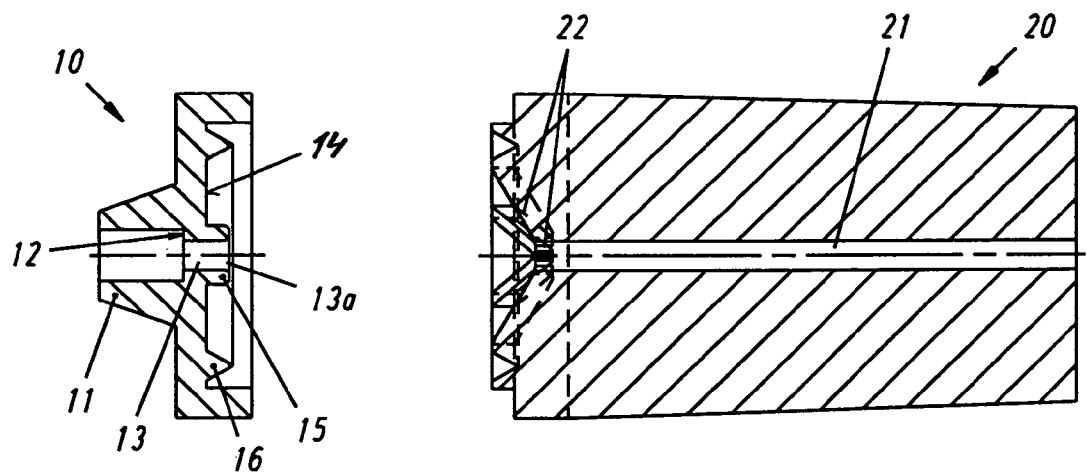
Figure 2:
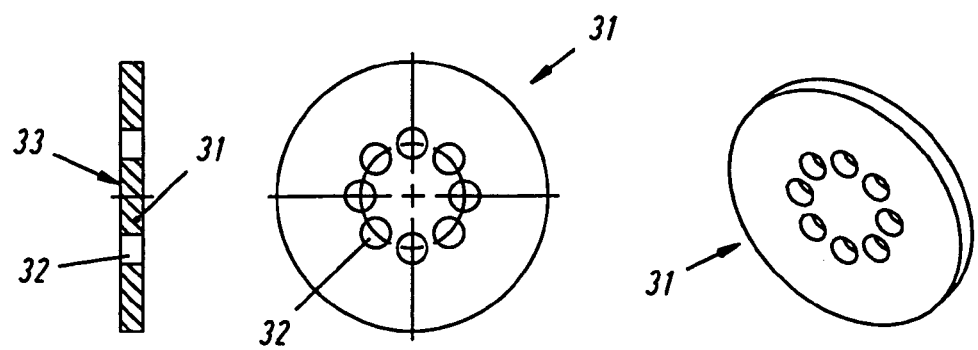

FIG. 2 shows a first embodiment of a connecting section including a valve. The connecting section of this embodiment is made up of two parts, a first upstream housing section 10 and a second downstream housing section 20. The complete housing 10, 20 is rotation symmetrical to its straight longitudinal center line, arranged in flow direction. A separating surface between the two housing sections 10 and 20 is positioned vertically to the flow direction. The separating surface accommodates a valve body 31 made of elastic material that is pressed by connecting the two housing sections 10 and 20 circumferentially along its outer peripheral edge between the two housing sections 10 and 20. The separating surfaces are thus sealed by the valve body 31. Furthermore, the circumference of the housing sections 10 and 20 is annually welded in position S. Subject to the material the valve body 31 is preferably incorporated in this welded connection.

The valve body 31 is formed by a circular membrane disc, possibly containing an axially protruding ring web. In its installed condition its central section serves as a valve disc. The circular valve disc is surrounded by one or several apertures 32. The outer annular section provides the said fixing between the two housing sections 10 and 20.

The two housing sections 10 and 20 both contain a central bore 13 and 21. The bores 13 and 21 are flush. In the bore of the first housing section 10 the connecting needle 7 is inserted and attached in an upstream housing cone 11. In order to achieve a swirl-free flow, the bore in the first housing section 10 is of a diameter corresponding to the external diameter in its upstream section and to the internal diameter of the needle 7 in its connected downstream section. This not only creates a feed line 13 with a continuous smooth wall, but also a shoulder 12 against which the downstream end of the needle 7 abuts. At the downstream end of the feed line 13 the first housing section 10 forms a web surrounding the line aperture 13a in form of a sealing lip 15, whose face is preferably rounded.

The valve body 31 is pretensioned over the circular sealing lid 15. For this purpose, the inside of the first housing section 10 tapers off against the direction of the flow from the sealing lip 15 protruding into the flow direction. The sealing lip 15 is thus surrounded by a tapered ring surface 14. Like the sealing lip 15, the circular area 14 is surrounded by a protruding annular ring 16 raised in the direction of flow from the annular surface 14 which is opposed by a respective recess on the side of the second housing section 20. Before assembling the two housing sections 10 and 20, the valve body 31 lies slightly distanced by the sealing lip 15 in its external circumference on the first housing section 10 and is therefore also slightly distanced from the circular surface 14. By pressing both the housing sections 10 and 20 together, the valve body disc 31 is bent over the sealing lip 15 towards the external circumference of the circular surface 14 and is thus simultaneously pretensioned on the sealing lip 15. The annular ring 16 pushes the valve body disc 31 into the recess of the second housing section 20, achieving an annular clamping of the valve body disc and simultaneously a good seal. The sealing lip 15 and the valve body 31 seal a flow cross section along the circumferential narrow contact area 33 which the sealing lip 15 presses against the valve body 31.

The design of the valve body 31 as a simple membrane disc and the arrangement of the sealing lip 15 on a comparatively rigid housing achieve particularly good reproducible valve characteristics as well as an easily produced elastic valve body 31. The downstream face of the first housing section 10 over which the valve body 31 is tensioned and said valve body 31 itself are dimensioned in such a way that the valve body 31 in the position shown in assembled condition in FIG. 2 is pressed with such a pre-tensioning force against the contact surface 33 by the sealing lip 15 that the application force in the contact surface 33 exceeds the pressure created in the device according to FIG. 1 by the fluid column at the maximum height differential H on the flow cross-section of the sealing lip.

When this maximum pressure of the fluid column is exceeded by a stipulated safety factor, the valve body 31 is lifted from its seat at the sealing lip 15. The insulin fluid can now flow through the feed line 13, around the sealing lip 15 and through one or several apertures 32 concentrically arranged around the sealing lip 15 within the valve body 31 and can flow downstream of the valve body 31 via the bore serving as outlet line 21 into the hose catheter. In the other direction, the valve represents a secure return-flow barrier.

Directly behind the valve body 31 a cavity is formed in the second housing section 20 into which the housing body 31 can expand. To avoid the rear downstream side of body 31 coming into contact with the internal wall of the second housing section 20 and possibly blocking the flow apertures 32, radially extending spacer fins 22 protrude from the internal wall of the second housing section 20 in the direction of the valve body 31.

Figure 3:
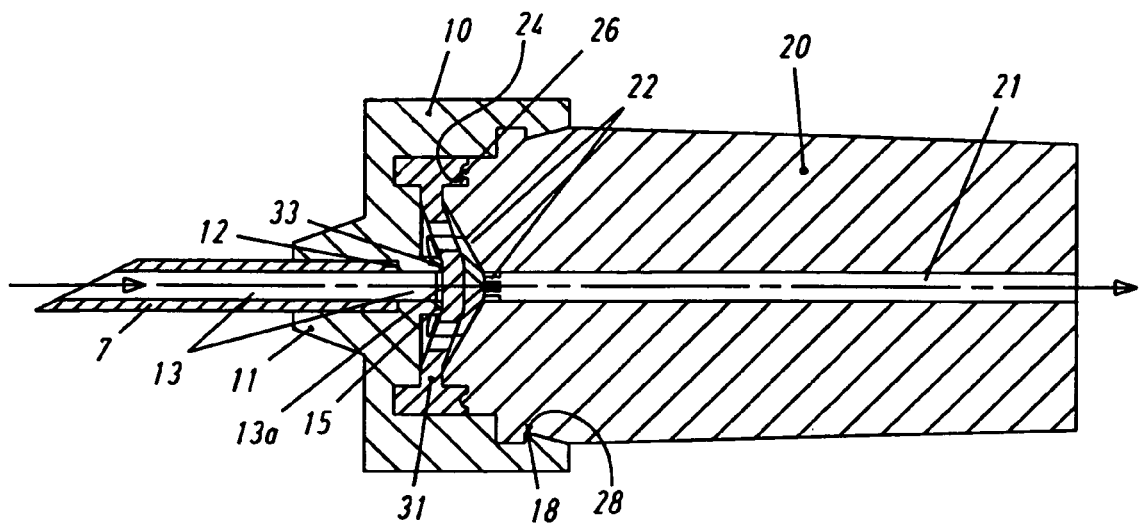
Figure 3:
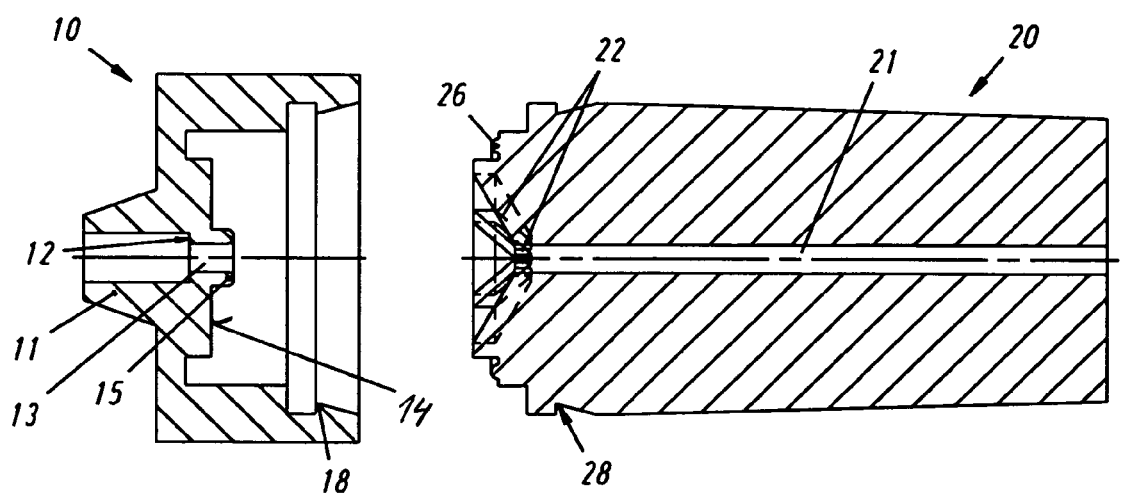
Figure 3:
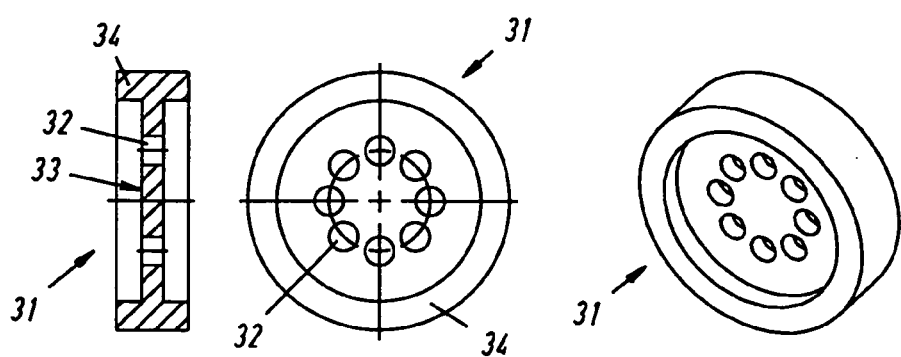

FIG. 3 shows an embodiment derived from the valve of FIG. 2. The function of the valve is the same as for the previous valve. The elastic valve body 31 is in this embodiment formed by a membrane with a double-T-shaped circular cross-section. The ring web 31 protruding from the outer circumference of the membrane disk on both sides, serves to secure the joints of both housing sections 10 and 20. At the same time, it represents a comparatively large forming mass for sealing the housing. In this embodiment both housing sections 10 and 20 are connected by a snap connection. For the snap connection, the second housing section 20 is inserted into the hollow cylindrical first housing section 10, opening on the downstream side and then locked. For this purpose, the second housing section 20 contains a groove 28 in its external circumference and the first housing section 10 contains a radial circumferential locking fin 18, radially protruding towards the inside, which engages into the groove 28.

Figure 4:
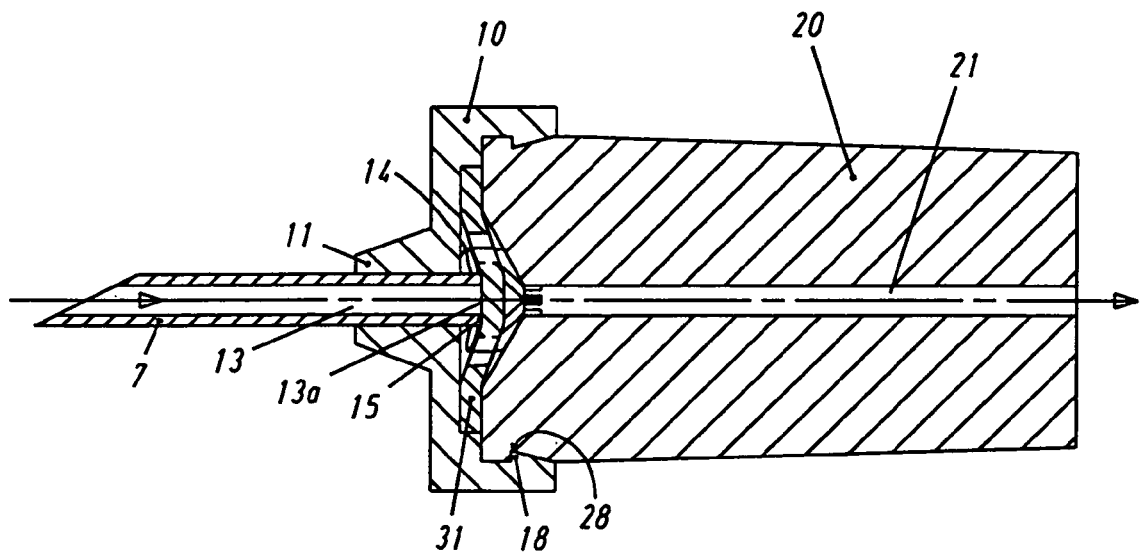
Figure 4:
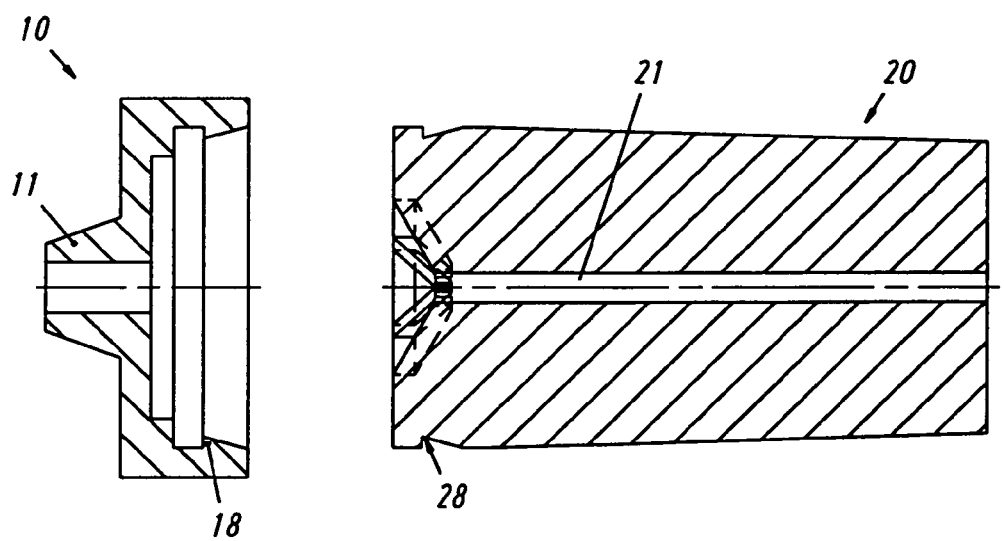
Figure 4:
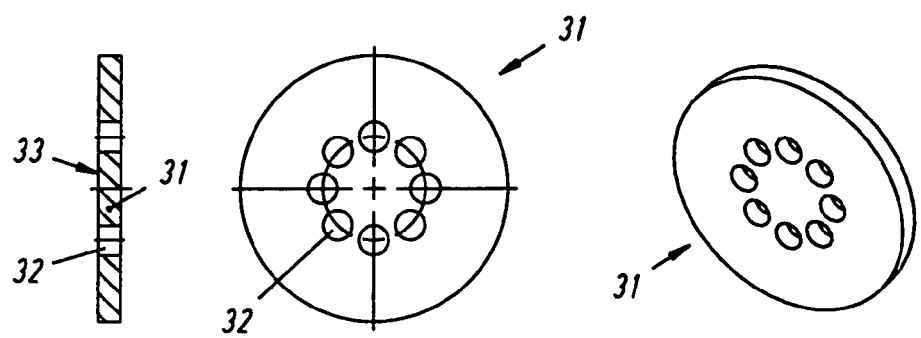

A third embodiment, in which the sealing lip is formed on the housing, is shown on FIG. 4. In this embodiment, the valve body 31, according to FIG. 2 is shown together with the snap connection shown, in principle, in FIG. 3. In the embodiment of FIG. 4, a simpler construction of the first housing section 10 is shown, in which the accommodation for the connecting needle 7 is formed by a simple bore into which, after the valve body 31 has been inserted in the first housing section 10 and both housing sections 10 and 20 have been snapped 16 together, the connecting needle 7 is inserted or pushed through up to a position relative to the surface 14 in which it tensions the subsequently inserted valve body 31 with the required tension force. For this purpose, the downstream end of the connecting needle 7 forms the sealing lip 15. It is therefore rounded so that the valve body 31 cannot be damaged. The retrospective insertion of the needle 7 can compensate for manufacturing tolerances of the valve body 31 as the needle 7 is inserted to precisely the point at which the desired application force of the valve body 31 to the sealing lip on the needle side is achieved. With regards to the further details we refer to the description relating to FIGS. 2 and 3.

Figure 5:
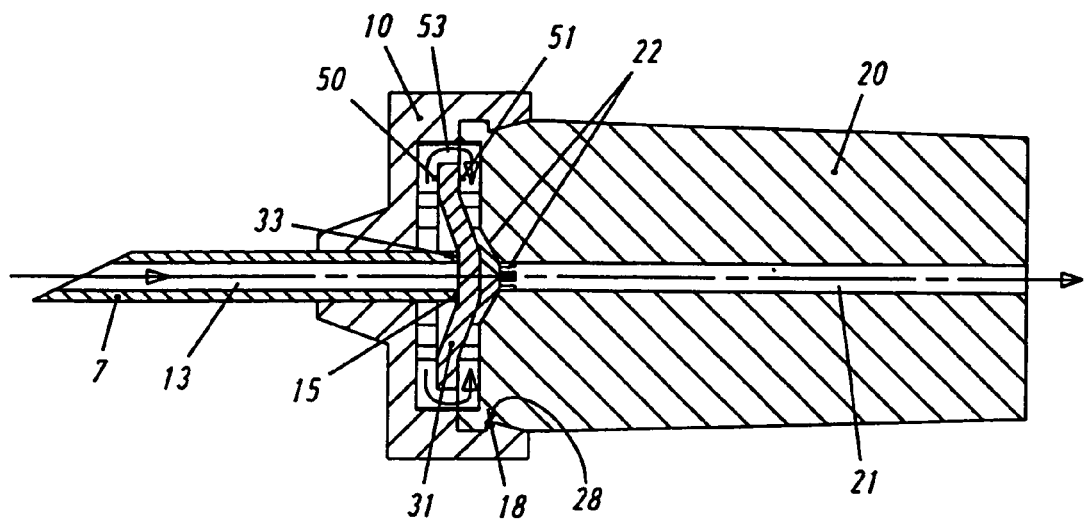
Figure 5:
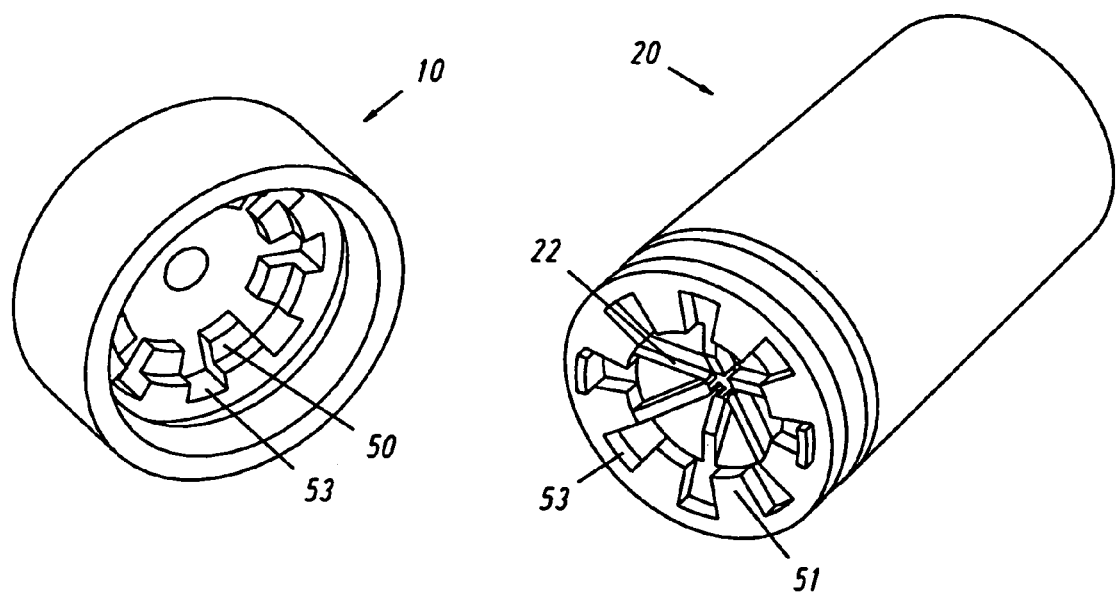
Figure 5:
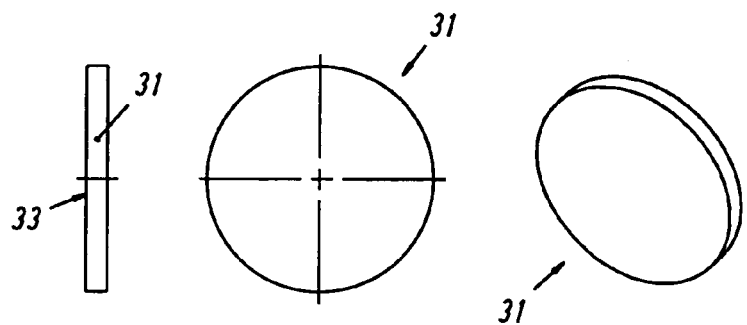

FIG. 5 also shows an embodiment in which the sealing lip 15 is provided on the housing side. As in the embodiment according to FIG. 4, said sealing lip is formed by the rear end of the connecting needle 7. In contrast to the aforementioned valve constructions, the valve body 31 consisting of a circular membrane disc punched out of elastic material, does not contain any apertures. The valve body 31 is no longer tensioned on a circular ring between the housing sections 10 and 20 but instead only on some circular segments 50 and 51, thus causing the fluid drug to be passed through the aperture channels 53 outside of the circular disc diameter of the valve body 31 and to the outlet bore 21.

The pre-tensioning of the valve body 31 is in this case also carried out after the valve body 31 is inserted into a housing part and both housing parts have been assembled, by inserting the connecting needle 7 into the upstream section of the housing 10 until the valve body 31 is pretensioned to such an extent that the desired piercing pressure for the valve is achieved.

If the fluid pressure in the feed line 13 exceeds the application force of the valve body 31 on the sealing lip 15, an annular flow gap is opened at the contact surface 33. The insulin fluid can flow through this annular gap and then through the aperture channels 53 of the valve body 31 and is discharged via the aperture line 21.

FIGS. 6 to 9 show further valve embodiments, in which the desired sealing or piercing characteristics are achieved with the aid of a sealing lip. In these embodiments the sealing lip is, however, provided on the elastic valve body 31. For these examples, we also refer to the above description. Only the different characteristics are explained.

Figure 6:
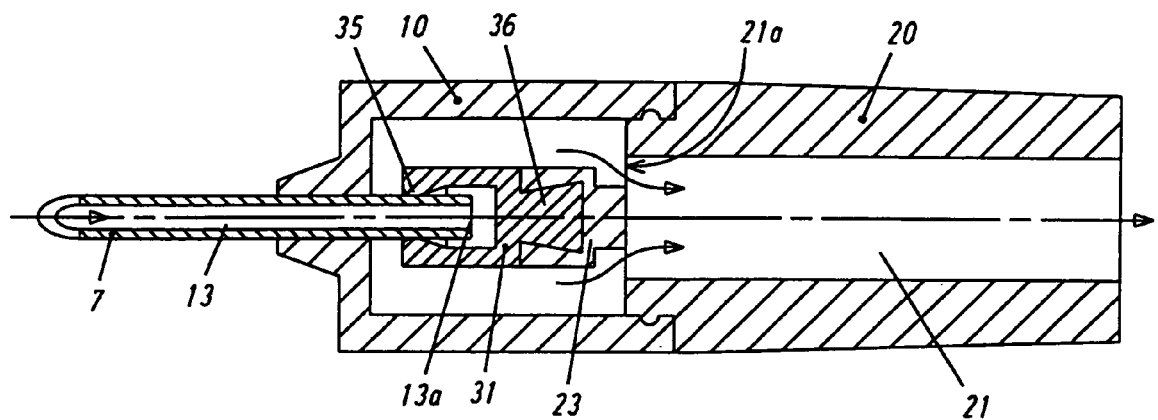
Figure 6:
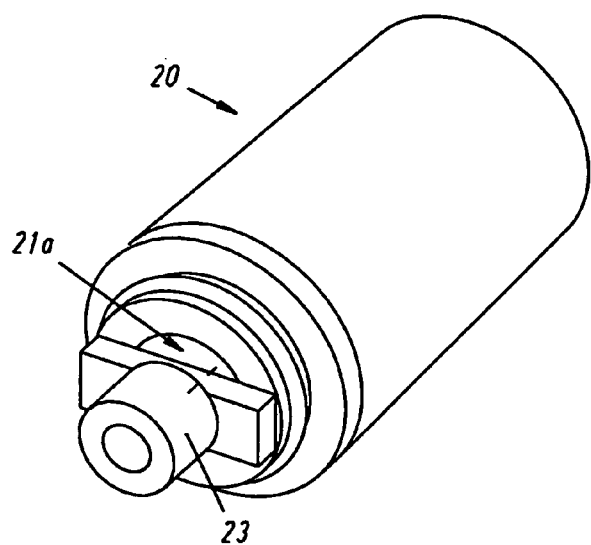
Figure 6:
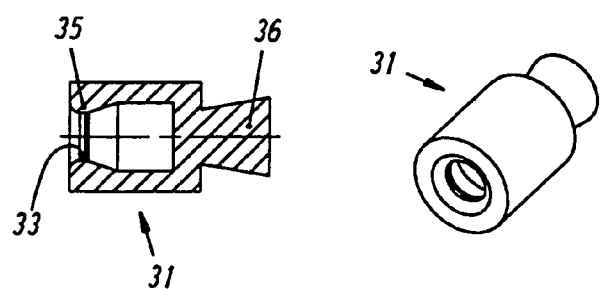

In the valve according to FIG. 6, the connecting needle 7 protrudes once again into the first housing section 10. On the second housing section 20 opposing the downstream aperture 13a of the connecting needle 7, the elastic valve body 31 is fixed with a downstream valve body extension 36 having a dove-tailed longitudinal section. The extension 36, which widens downstream, is seated in a flange-like holding section 23 protruding from the second housing section 20 towards the connecting needle 7. The valve body 31 is shaped like a pot opening towards the direction of flow. At the upstream edge of the pot a circumferential sealing lip 35 radially protrudes towards the inside. When installed, this sealing lip 35 seals around the external surface of the connecting needle 7. Only when the fluid pressure on the inside of the pot exceeds the pressure exerted on the contact surface 33 formed by the pretension force on the external surface of the connecting needle 7, a gap is released along this contact surface through which the fluid from the feed line 13 can flow into the recess in the housing 10, 20 around the pot-like valve body 31. The housing cavity is connected to the outlet line 21 in the second housing section 20 via one or several and in the embodiment two apertures 21a, which are not covered on the base of the valve body support 23.

The embodiment according to FIG. 7 shows a particularly simple housing design. The second housing section 20 consists of a hollow cylinder with a large upstream aperture and a discharge bore 21 centrally connected to it. The valve body 31 is accommodated in the aperture. The first housing section 10 is a circular cylindrical assembly insert, holding the connecting needle 7 and which is screwed in or fixed in other ways in the aperture of the second housing section 20.

The valve body 31 is attached to the holding section 23 in a similar way as shown in FIG. 6. The valve body has a mushroom shape. The curved mushroom surface faces against the direction of flow. At its downstream circumference, the curved mushroom surface is pretensioned as a sealing lip 35 against the internal wall 24 of the aperture bore in housing 20.

FIG. 8 shows an embodiment with an approximate hollow semi-spherical valve body 31. The valve body 31 is attached to the housing in the same way as the valve bodies of FIGS. 6 and 7. The housing corresponds to the housing of FIG. 7. The valve body 31 is pressed with its upstream, circumferential face, forming the contact surface 33 against a simple planar counter surface of the assembly insertion section 10 surrounding the downstream aperture 13a of the feed line 13. The valve body 31 provides a bell-shaped seal for feed line 13.

Figure 9:
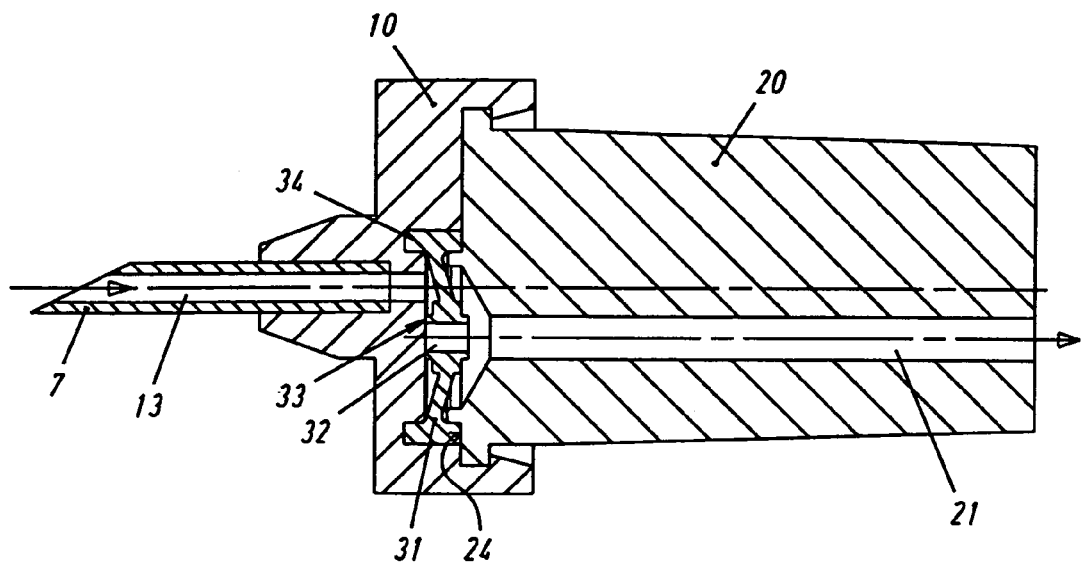
Figure 9:
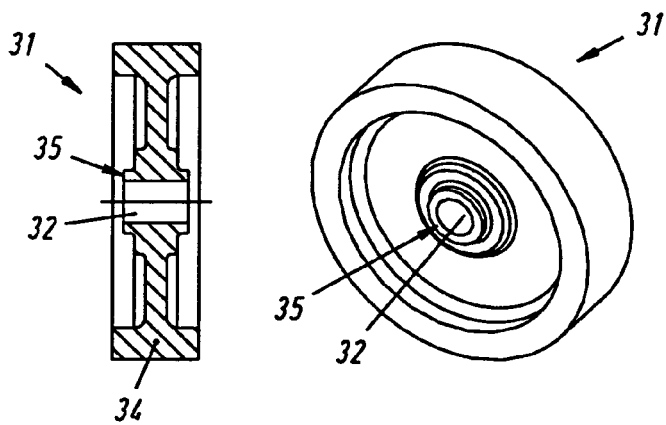

The valve body 31 used for the embodiment according to FIG. 9 differs from the previously described embodiment mainly by the fluid pressure being generated not within the sealing lip 35 but in a circular area around this sealing lip 35.

In the valve body 31 according to FIG. 9 the central aperture 32—preferably a simple bore—is enclosed by a sealing lip 35. The sealing lip 35 is surrounded by a tapered circular area which in turn is surrounded by ring web 34 protruding from the tapered ring surface in the same direction as the sealing lip 35. Preferably the sealing lip 35 has been tapered itself in relation to the ring web 34. In order to be able to pretension the valve body 31, an annular groove in the downstream face of the first housing section 10 is formed deeper than the distance between the faces of the external ring web 34 and the sealing lips 35 in the initial condition of the valve body 31. Upon positioning the external ring web 34 into the receiving groove of the first housing section and pressing the ring web fully into this groove, the sealing lip 35 is pressed against the planar surface of the first housing section 10 surrounded by the ring groove. The feed line 13 in the first housing section 10 is not centered in this embodiment. It ends at the downstream face within the tapered ring web at a point between the sealing lip 35 and the ring web 34 of the valve body 31. In this way, an annular pressure area is formed. If the application pressure of the sealing lip 35, created by the elastic pretensioning of the valve body 31, is exceeded in this annular area, the sealing lip 35 is lifted off its counter face. A flow is then facilitated from the feed line 13 to the outlet line 21 via the circular area and the bore 32.

Figure 10:
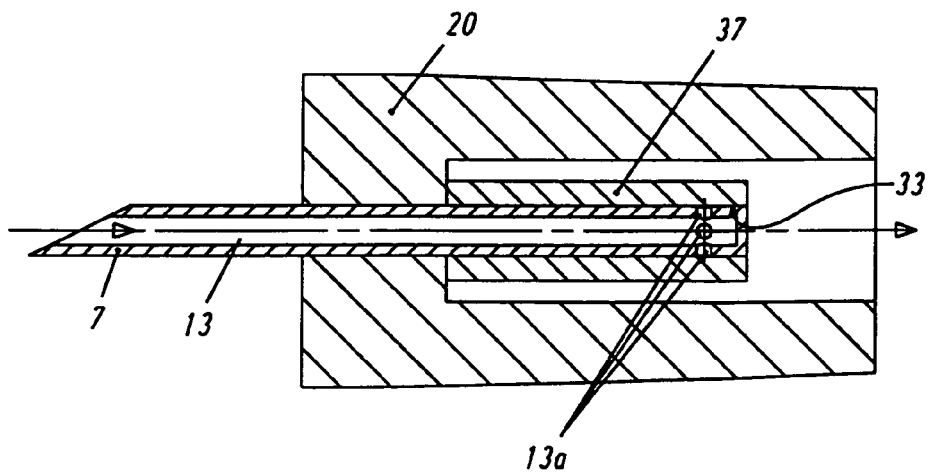
Figure 11:
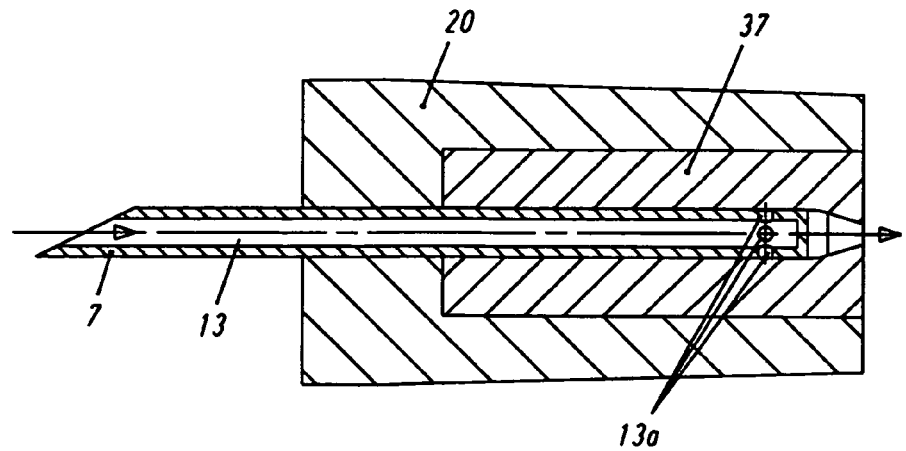

FIGS. 10 and 11 show valves similar to bicycle tube valves. The valve bodies 37 are formed by hose sections. Both embodiments have a single-section housing 20. The respective valve body 37 can be retained on the needle 7 or in the housing 20 or between both of these elements due to its functional design.

In FIG. 10 a simple hose section 37 is placed on the downstream end of the feed line 13. In this embodiment said end is formed by the connecting needle 7. On its face, the feed line 13 is closed at its downstream end. The feed line 13 contains one or several radial apertures 13a in its end section protruding into the housing 20, which are surrounded and consequently sealed by the hose-like valve body 37. The face seal of the feed line 13 could also be formed by the sack-like valve body 37, to produce the feed line 13 by cutting it from an endless hollow needle.

In the embodiment according to FIG. 10 the cavity in housing 20 is lined with an elastic sealing material 37. After the lining, the feed line 13 is pushed through the sealing material. If necessary, the sealing material can also be pre-pierced to facilitate the introduction of the feed line 13.

Figure 12:
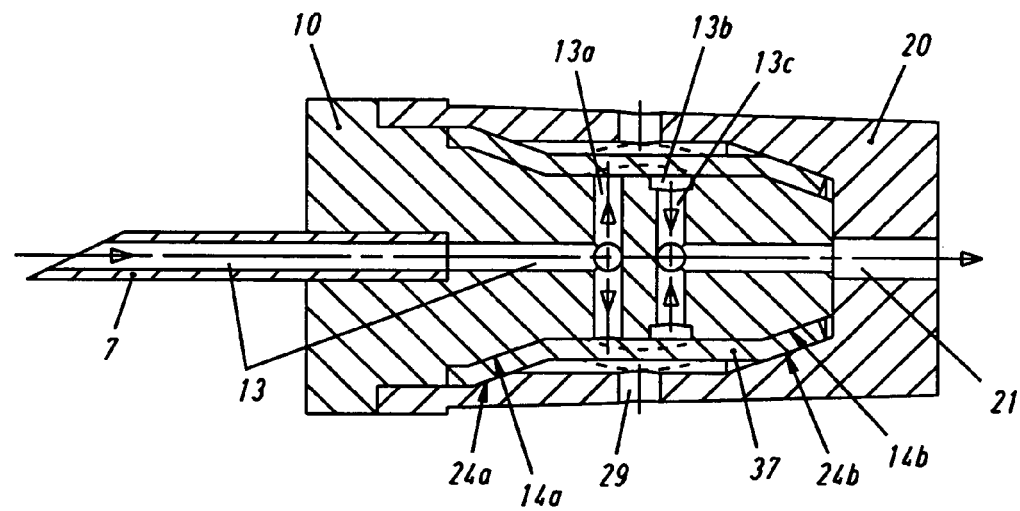
Figure 12:
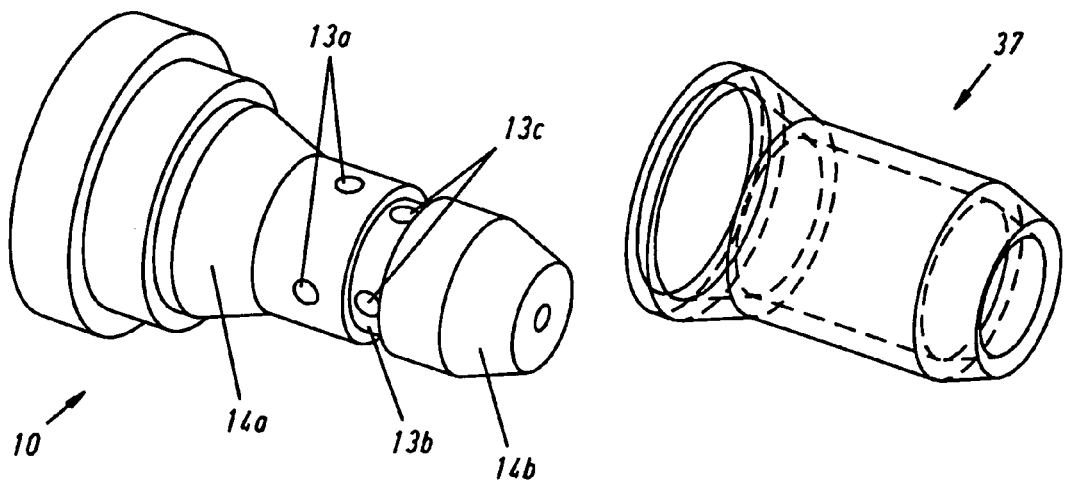

In FIG. 12 a two-section housing 10, 20 is shown in connection with the hose-like valve body 37. The fluid from the ampule passes via a feed line 13 and via at least one connection 13a—preferably a connection bore—to the external surface of the first housing section. Downstream of the connection 13a, at least one further connecting channel 13c is arranged at the external surface of the first housing section 10, ending in groove 13b. At least one further connecting channel 13c leads to the outlet line 21 in the catheter. The connection bore 13a and the groove 13b are separated by an intermediate web formed by the outer surface of the first housing section. The valve body 37 is tightly tensioned around the outer surface of the first housing section 10 and forms a seal between the connecting bore 13a and the groove 13b. The groove 13b is preferably a circumferential groove.

The embodiment of FIG. 12 shows a particularly good external seal at the sealing surfaces 14a, 24a and 14b, 24b. In these sealing areas, the first and second housing sections 10, 20 are provided with matching conical surfaces 14a, 24a and 14b, 24b in between which the upstream and the downstream end of the valve body 37 are clamped when joining the housing sections. The connecting bore 13a, the interim web and the groove 13b leave sufficient room in the second housing section 20 for the valve body 37 to expand in order to create the flow connection between the connection bore 13a and the groove 13b once the pretension pressure has been exceeded. The dotted lines show the expanded condition of the valve body 37. The second housing body 20 contains the pressure compensation aperture 29, so that ambient pressure always exists around the outside of the valve body 37.

Figure 13:
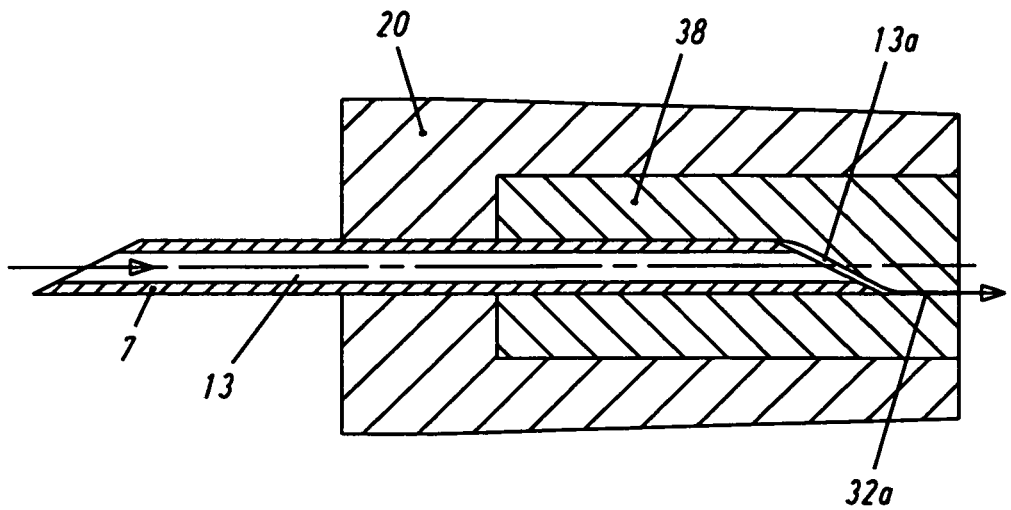

FIG. 13 shows a single-section housing 20 comparable to FIGS. 10 and 11, containing a narrow first bore in its upstream section and, in comparison, a wider second bore in its downstream section. The first bore ends in the second and serves as a narrow guide and seat for the connecting needle 7. A valve body in form of a simple sealing stopper 38 has been pressed or cast into the wider downstream bore. The valve is created during the insertion of the connecting needle 7, during which the connecting needle 7 fully pierces the sealing stopper 38 and is then pulled out a little after the piercing operation. In this way an aperture 32a is created in the sealing stopper 38. The valve of FIG. 13 has the advantage that the connecting needle 7 or the feed line 13 can be created by simply cutting them from a continuous hollow needle.

Figure 14:
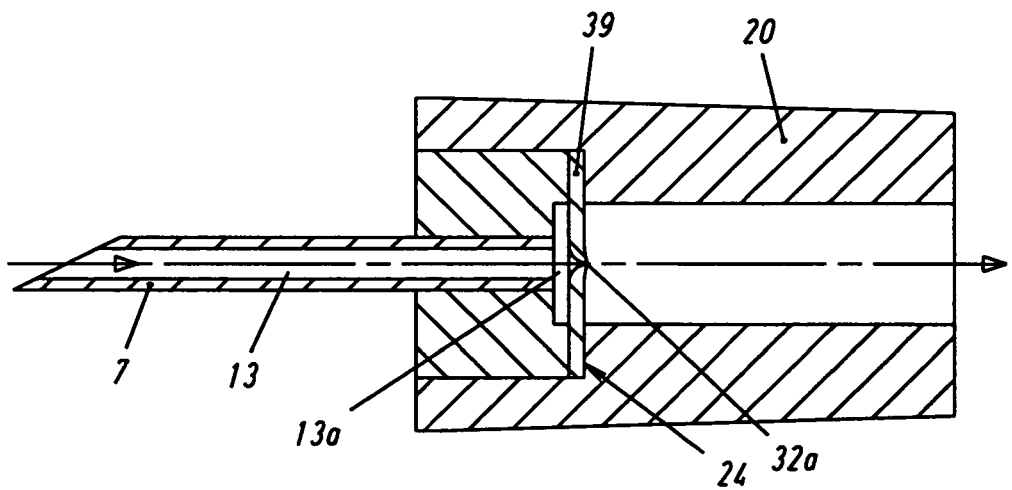
Figure 14:
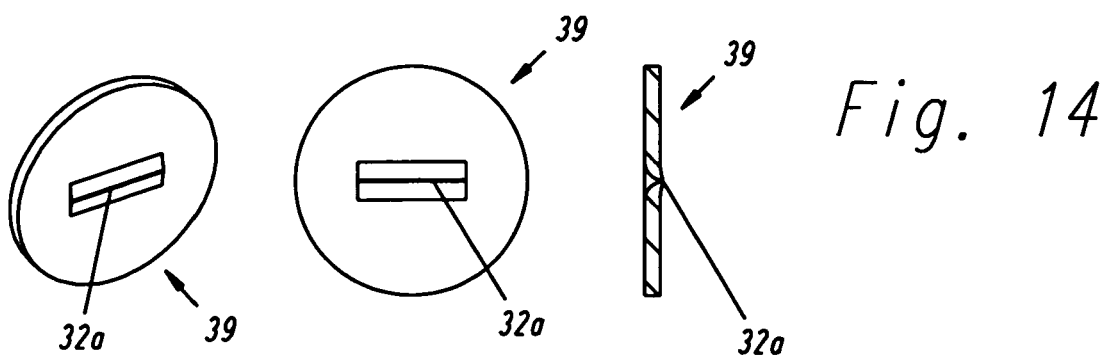
Figure 15:
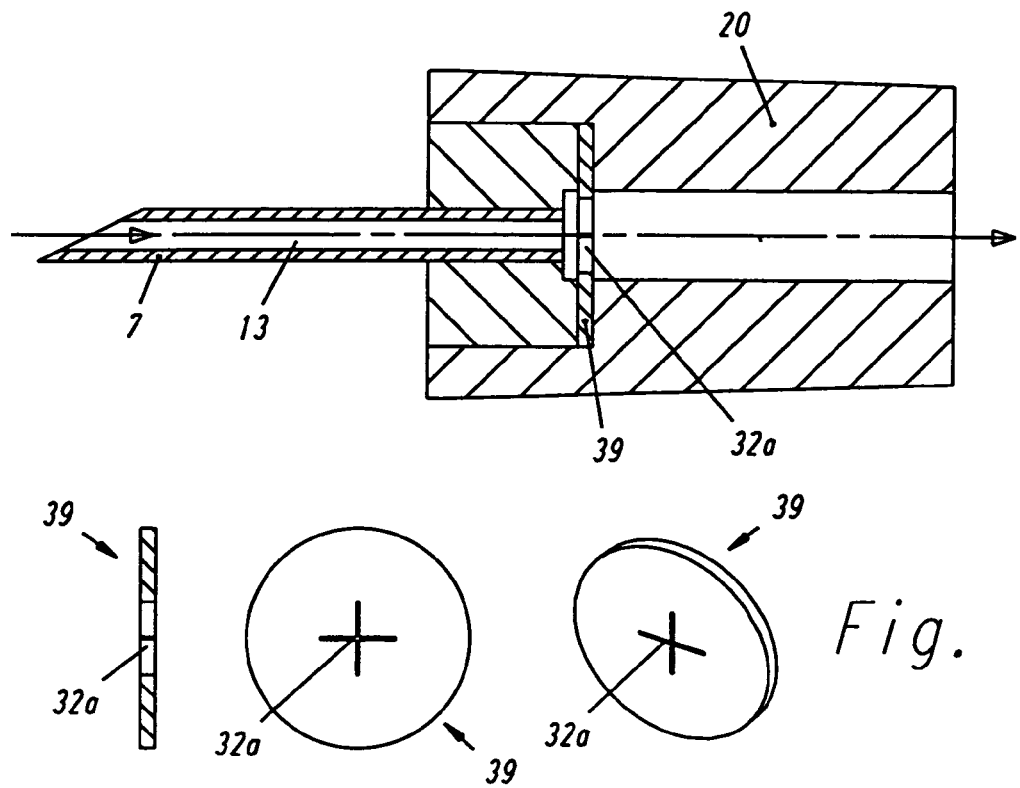
Figure 16:
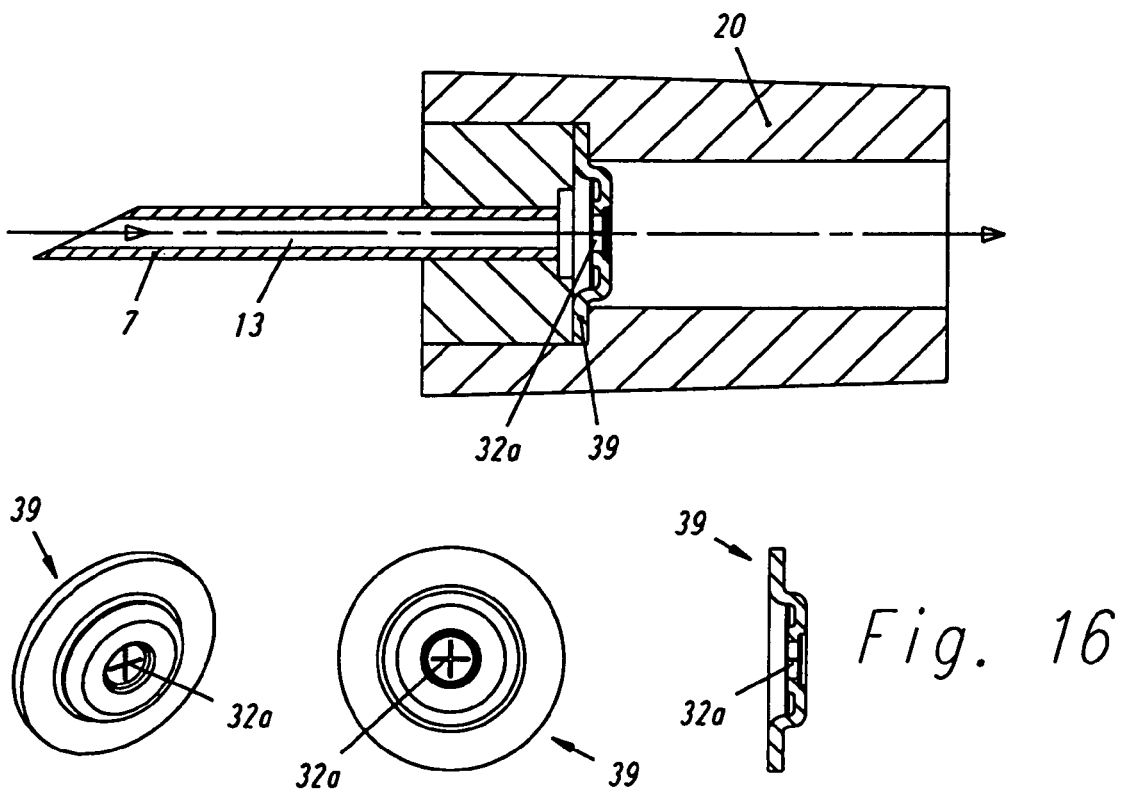

The embodiments according to FIGS. 14 to 16 show valves operating in a manner of a heart valve. The valve bodies 39 of FIGS. 14 and 15 are formed by simple circular discs, incorporating slits 32a. The housings contain an assembly insertion section 10 for insertion into the second housing section 20 with a simple inlet bore, which optionally ends in the outlet bore in the second housing section 20 via an interim stage. The downstream face of the assembly insertion section 10 presses the valve bodies 39 against the shoulder in the housing section 20 surrounding the transition between the inlet and outlet bore.

Whilst the valve body 39 of FIG. 14 only contains a slit with sealing lips 32a formed in the direction of flow, the valve seat 39 of FIG. 15 contains two cross slits 32a.

In the arrangement according to FIG. 16, a cavity is arranged in the housing 20 directly downstream of the valve body 39, into which the valve body 39 can expand. This valve body 39 also contains slits. As a result of the fluid pressure, the valve body fills like a bubble until it finally opens. It is less rigid than the valve body 39 described in FIGS. 14 and 15.

FIGS. 17 to 21 show valves whose elastic valve body 41 is tensioned by pressure springs to achieve the desired valve effect.

Figure 17:
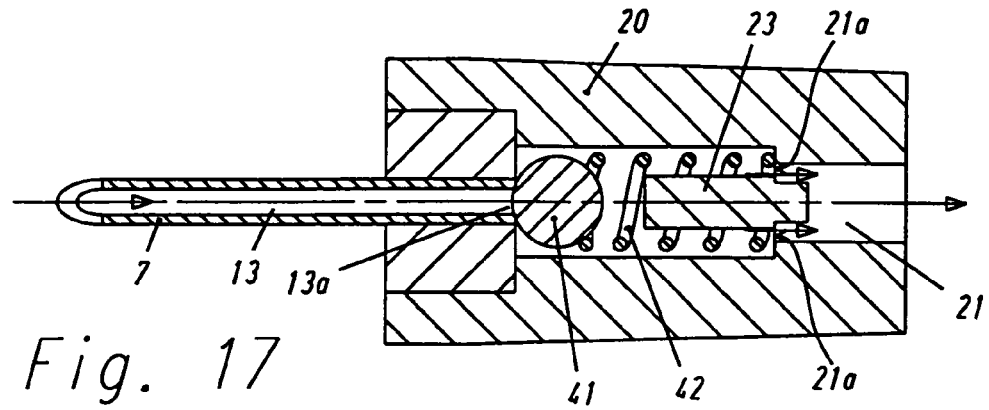

The valve body 41 of the valve according to FIG. 17 is spherical and is pressed by a pressure spring 42 against the direction of flow into the downstream aperture 13a of the feed line 13 serving as valve seat. The pressure spring 42 is passed through a central cylinder 23 of housing 20 pointing to the downstream aperture of the feed line 13. At its downstream end the cylinder 23 contains a flange with an aperture 21a through which the fluid flows into the outlet line 21 after opening the valve.

Figure 18:
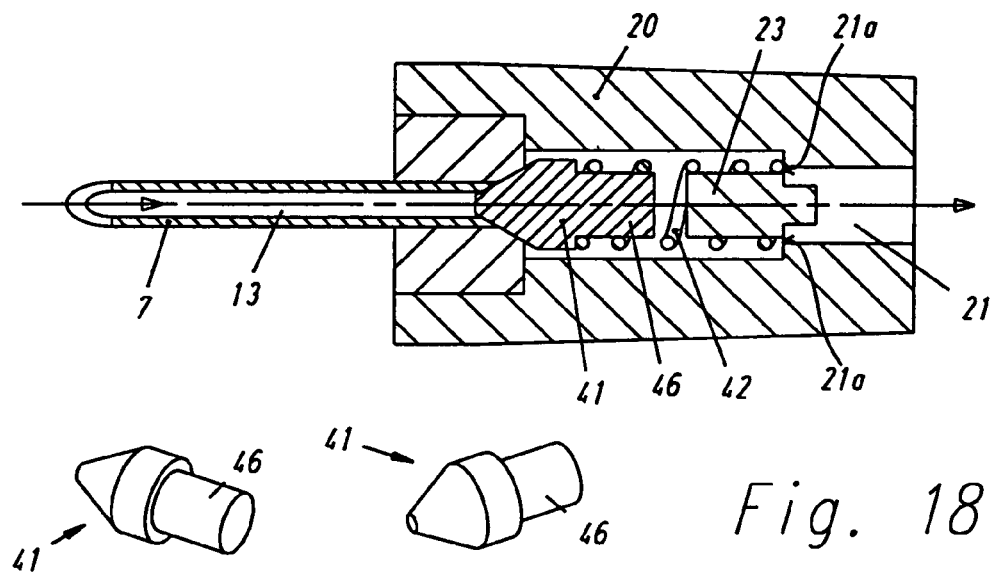
Figure 19:
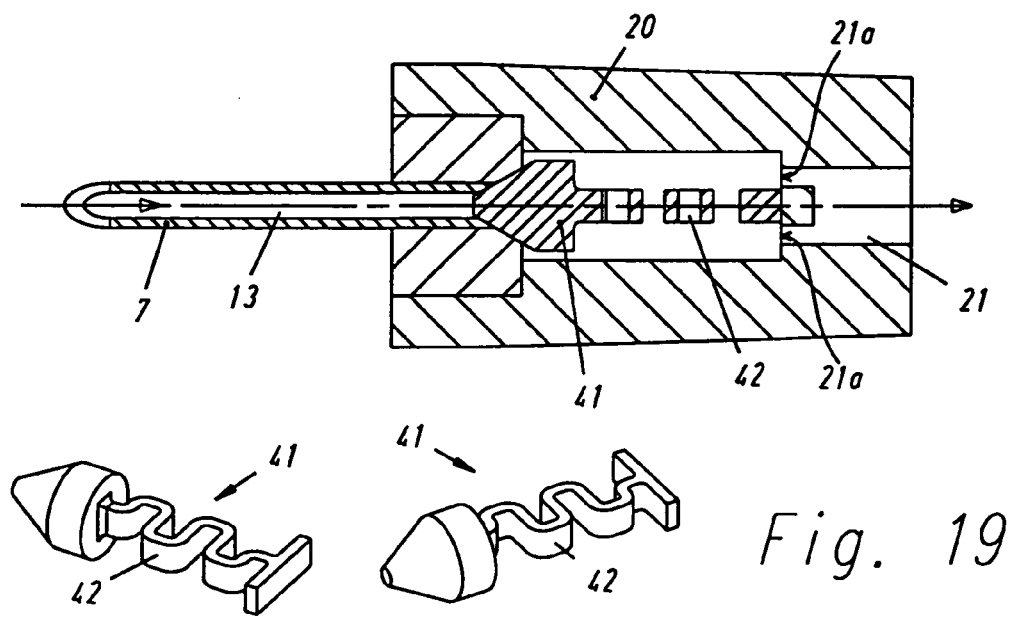

FIG. 18 shows an arrangement similar to that of FIG. 17. The valve body 41 of FIG. 19 has a conical shape at its upstream end. The downstream aperture of the feed line 13, forming the valve seat, also expands in the same conical manner. Furthermore the downstream end of the valve body 41 contains a cylindrical extension 46, guiding the pressure spring 42 at the valve body 41.

The valve body 41 of FIG. 19 once again presses its conical surface into the valve seat formed by the aperture in the feed line 13. The application pressure is generated by the plastic spring 42.

Figure 20:
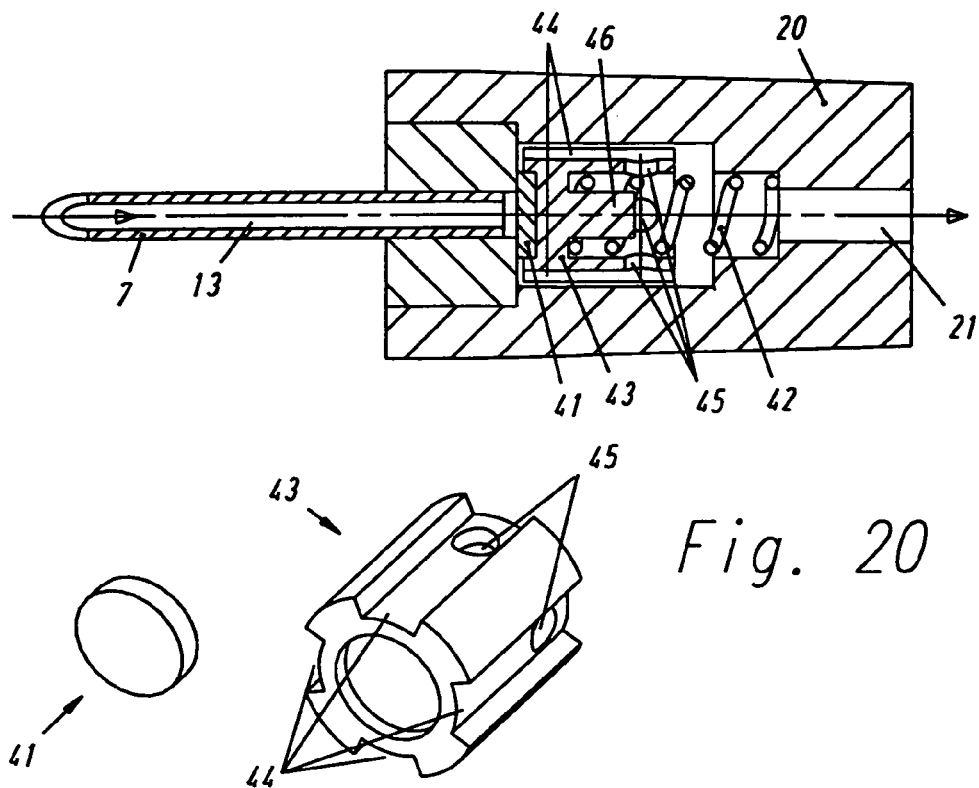

In FIG. 20 the valve body 41 is preferably a simple disc, secured at the upstream face of a cylindrical guide body 43. The guide body 43 contains longitudinal grooves 44 in its external surface. The guide body 43 is a hollow cylinder with a cylinder base at the upstream end on which the valve body 41 is positioned and to which it is fixed and from which an internal guide extension 46 protrudes into the direction of the flow. Via this guide extension 46 the pressure spring 42 is tensioned. The guide body 43 contains radial apertures 45 in its longitudinal grooves 44 through which the fluid drug can flow into the inside of the hollow cylindrical guide body 43 and from there through the outlet line 41 into the catheter.

Figure 21:
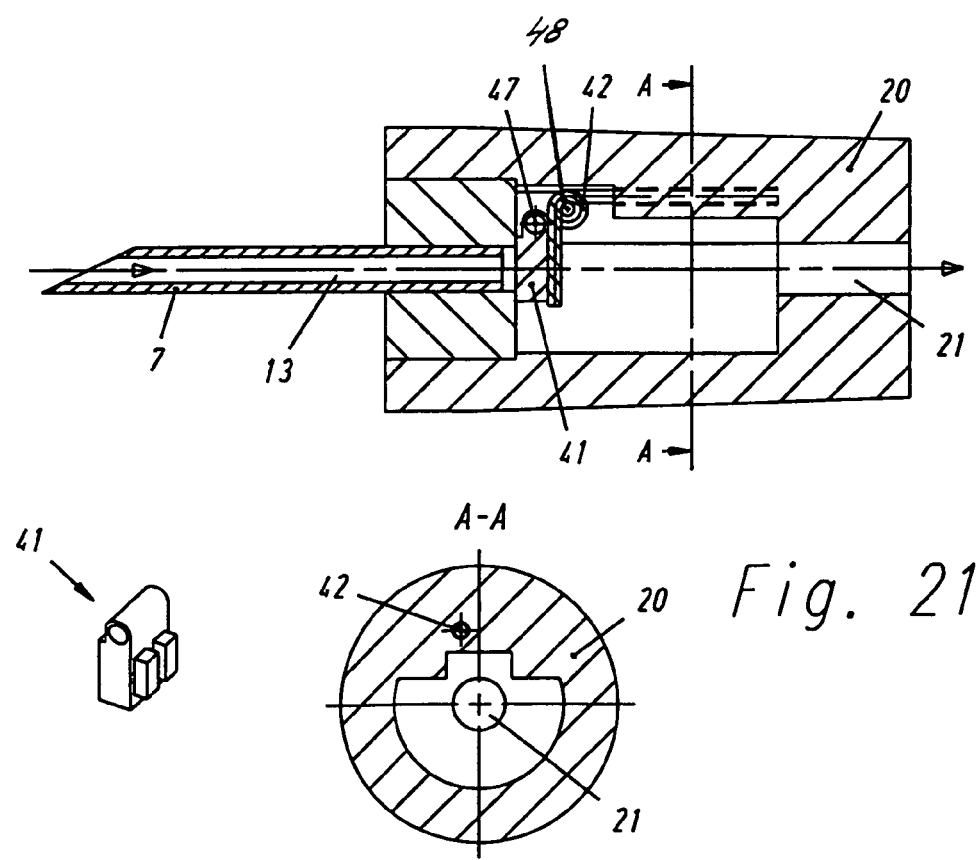

In the valve of FIG. 21 the valve body 41 is arranged as a flat valve around a rotary axis 47, laterally to the flow direction and directly at the downstream aperture of the feed line 13. At its rear downstream side, this return flap 41 is tensioned by a leg spring 42 for the closing of the feed line aperture. The leg spring 42 is inserted into the housing section 20 in such a way that its spring axis 48 is parallel to the return flap rotary axis 47, with the first leg of the L-shaped spring 42 pressing against the rear side of the return flap 41 and the second leg pressing against the internal wall of the housing 20 serving as counter-section. The spreading force of the angled leg spring 42 securely presses the return flap 41 against the downstream aperture of the feed line 13. The second spring leg protrudes into an axial bore in the second housing section 20 and the first leg is inserted into a groove at the rear of the valve body 41; it may also be rigidly attached to the valve body 41. The spring axis 48 is formed only by the leg spring 42 which requires no further counter-section at 48.

The described combinations of valve bodies and housings can also be used with other combinations of the described housings and valve bodies.

We claim:

1. A device for administering in doses, in particular infusing, a medicinal liquid, comprising:
   a) a housing comprising a housing connecting section comprising a proximal end and a distal end, and a container from which the medicinal liquid is displaced through an outlet in doses, to be administered, wherein the housing connecting section connects the outlet to a catheter, the catheter having a front end that is or can be connected to an administering needle, wherein the rear end of the catheter is attached to the proximal end of the housing connecting section, the distal end of the housing connecting section is screwed in or on or fixed with a snap-in lock to an outlet section which extends the outlet, and wherein the proximal end of the housing connecting section and the distal end of the housing connecting section are connected by a thread or a snap-fit connection;
   b) a valve positioned in the housing connecting section and arranged in a flow cross-section of the medicinal liquid, and which in order to prevent self-emptying only allows a through-flow towards the end of said catheter when the liquid pressure acting in this direction is greater than a pressure bearing on said valve as a result of the inherent weight of a liquid column in the device, wherein
   c) the medicinal liquid is displaced through the outlet by advancing a stopper; and
   d) the housing connecting section is detachably connected to the outlet and carries a connecting needle such that said connecting needle pierces a membrane sealing the outlet when the housing connecting section is connected.

2. The device as set forth in claim 1, wherein the valve comprises a valve body having a biasing force against at least one opening of a supply line for the medicine fluid which leads to the valve body, wherein the magnitude of the biasing force is selected such that it generates a force on a contact area of the valve body which encompasses the opening, forming a seal, said force being greater than the force exerted on the charged valve cross-section by the fluid column.

3. The device as set forth claim 2, wherein the contact area is formed on a sealing lip encompassing the opening.

4. The device as set forth in the claim 3, wherein the valve body is tensed above the sealing lip towards a wall, upstream of the sealing lip, of a fluid-tight housing connecting section accommodating the valve body.

5. The device as set forth in claim 3, wherein the sealing lip is formed on the supply line.

6. The device as set forth in claim 3, wherein the sealing lip presses transverse to the flow direction against a circumferential area encompassing the flow cross-section.

7. The device as set forth in claim 2, wherein the valve body encompasses a surface area of the supply line and the region of the supply line encompassed by the valve body is provided with the at least one opening forming the flow cross-section.

8. The device as set forth in claim 1, wherein the valve does not allow the flow until the fluid pressure exceeds the maximum possible pressure of the fluid column.

9. The device as set forth in claim 8, wherein the valve does not allow the flow until the fluid pressure exceeds the maximum possible fluid pressure of 0.3 bar.

10. The device as set forth in claim 1, further comprising an outlet support associated with the container, wherein the connector casing housing connecting section is fixed to the outlet support.

11. The device as set forth in claim 1, wherein the valve comprises a passive unidirectional valve.

12. The device as set forth in claim 1, wherein the connector casing is fastened to an outlet support of the container which lengthens the outlet.

* * * * *

UNITED STATES PATENT AND TRADEMARK OFFICE
CERTIFICATE OF CORRECTION

PATENT NO. : 7,291,133 B1  Page 1 of 1
APPLICATION NO. : 09/092546
DATED : November 6, 2007
INVENTOR(S) : Beat Kindler et al.

It is certified that error appears in the above-identified patent and that said Letters Patent is hereby corrected as shown below:

SPECIFICATION

| Column | Line | PTO | Should Read |
|---|---|---|---|
| 3 | 62 | "secured 21 on a rack" | -- secured on a rack -- |
| 6 | 28 | "snapped 16 together" | -- snapped together -- |
| 7 | 57 | "Lip 35," | -- Lip 35. -- |

CLAIMS

| Column | Line | PTO | Should Read |
|---|---|---|---|
| 12 | 10 | "connector casing housing connecting section" | -- housing connecting section -- |

Signed and Sealed this

Eighth Day of July, 2008

JON W. DUDAS
*Director of the United States Patent and Trademark Office*